(12) United States Patent
Gulachenski

(10) Patent No.: US 9,764,111 B2
(45) Date of Patent: *Sep. 19, 2017

(54) CATHETER MARKERS

(71) Applicant: MicroVention, Inc., Tustin, CA (US)

(72) Inventor: Joseph Gulachenski, Trabuco Canyon, CA (US)

(73) Assignee: MicroVention, Inc., Tustin, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/243,926

(22) Filed: Aug. 22, 2016

(65) Prior Publication Data

US 2016/0354578 A1  Dec. 8, 2016

Related U.S. Application Data

(63) Continuation of application No. 14/042,145, filed on Sep. 30, 2013.

(60) Provisional application No. 61/708,553, filed on Oct. 1, 2012.

(51) Int. Cl.
| | |
|---|---|
| *A61M 25/098* | (2006.01) |
| *A61M 25/00* | (2006.01) |
| *A61B 17/12* | (2006.01) |
| *A61M 25/01* | (2006.01) |
| *A61M 25/10* | (2013.01) |
| *A61B 90/00* | (2016.01) |

(52) U.S. Cl.
CPC ..... *A61M 25/0012* (2013.01); *A61B 17/1214* (2013.01); *A61M 25/0108* (2013.01); *A61M 25/10* (2013.01); *A61B 2090/3966* (2016.02); *A61M 25/005* (2013.01); *A61M 2025/1079* (2013.01); *Y10T 29/49826* (2015.01)

(58) Field of Classification Search
CPC ............ A61M 25/005; A61M 25/0012; A61M 2025/09083; A61M 25/0108; A61M 2205/32
USPC .......................... 604/524, 526, 529
See application file for complete search history.

(56) References Cited

U.S. PATENT DOCUMENTS

| | | | | |
|---|---|---|---|---|
| 4,932,419 | A | * | 6/1990 | de Toledo ....... A61M 25/09025 600/434 |
| 5,084,022 | A | * | 1/1992 | Claude .................. A61M 25/09 600/585 |
| 5,606,981 | A | | 3/1997 | Tartacower et al. |
| 5,724,989 | A | * | 3/1998 | Dobson ................. A61M 25/09 600/585 |
| 5,951,539 | A | * | 9/1999 | Nita ..................... A61M 25/005 604/524 |
| 6,152,912 | A | | 11/2000 | Jansen et al. |
| 6,217,566 | B1 | * | 4/2001 | Ju ....................... A61M 25/005 604/526 |
| 6,235,050 | B1 | | 5/2001 | Quiachon et al. |
| 6,520,934 | B1 | | 2/2003 | Lee et al. |
| 7,065,394 | B2 | * | 6/2006 | Hobot .................... A61L 29/02 600/424 |

(Continued)

OTHER PUBLICATIONS

United States Patent and Trademark Office, Office Action mailed May 16, 2016 in U.S. Appl. No. 14/042,145, 5 pages.

(Continued)

*Primary Examiner* — Gerald Landry, II
(74) *Attorney, Agent, or Firm* — Inskeep IP Group, Inc.

(57) ABSTRACT

A catheter is described having one or more markers and one or more marker sections.

14 Claims, 2 Drawing Sheets

(56) References Cited

U.S. PATENT DOCUMENTS

| | | | |
|---|---|---|---|
| 7,850,623 B2* | 12/2010 | Griffin | A61M 25/0013 600/585 |
| 7,905,877 B1* | 3/2011 | Jimenez | A61M 25/0012 604/523 |
| 8,157,780 B2 | 4/2012 | Lira et al. | |
| 2003/0009184 A1 | 1/2003 | Pepin | |
| 2004/0059258 A1 | 3/2004 | Campion et al. | |
| 2004/0073158 A1* | 4/2004 | Shah | A61L 29/02 604/19 |
| 2005/0255317 A1 | 11/2005 | Bavaro et al. | |
| 2006/0259011 A1* | 11/2006 | Kubo | A61M 25/0045 604/526 |
| 2007/0208405 A1* | 9/2007 | Goodin | A61F 2/95 623/1.11 |
| 2008/0015499 A1* | 1/2008 | Warnack | A61F 2/958 604/103.1 |
| 2009/0036833 A1 | 2/2009 | Parins | |
| 2010/0010476 A1* | 1/2010 | Galdonik | A61B 17/221 604/529 |
| 2010/0160899 A1 | 6/2010 | Gulachenski et al. | |
| 2012/0232478 A1 | 9/2012 | Haslinger | |
| 2012/0245521 A1 | 9/2012 | Gulachenski et al. | |
| 2012/0283700 A1* | 11/2012 | Pawluk | A61M 25/09 604/528 |
| 2013/0197353 A1* | 8/2013 | Von Oepen | A61M 25/0108 600/424 |

OTHER PUBLICATIONS

United States Patent and Trademark Office, Final Office Action mailed Jul. 28, 2015 in U.S. Appl. No. 14/042,145, 8 pages.
United States Patent and Trademark Office, Office Action mailed Jan. 21, 2015 in U.S. Appl. No. 14/042,145, 8 pages.
United States Patent and Trademark Office, Final Office Action mailed Sep. 23, 2014 in U.S. Appl. No. 14/042,145, 8 pages.
United States Patent and Trademark Office, Office Action mailed May 12, 2014 in U.S. Appl. No. 14/042,145, 17 pages.
WIPO, U.S. International Search Authority, International Search Report and Written Opinion mailed Dec. 16, 2013 in International Patent Application No. PCT/US2013/062855, 8 pages.

* cited by examiner

CATHETER MARKERS

RELATED APPLICATIONS

This application is a continuation of and claims priority to U.S. patent application Ser. No. 14/042,145 filed Sep. 30, 2013 entitled Catheter Markers, which claims priority to U.S. Provisional Application Ser. No. 61/708,553 filed Oct. 1, 2012 entitled Catheter Markers, both of which are hereby incorporated herein by reference in their entireties.

BACKGROUND OF THE INVENTION

Catheters may utilize radiopaque material on particular sections of the catheter to aid in imaging of the device while it is in the vascular system. Balloon catheters, embolic delivery catheters, and balloon catheters for embolic delivery are a few examples. Embolic delivery catheters typically utilize markers at the distal end of the catheter, and at a point 3 centimeters from the distal end to aid in imaging and embolic delivery. Balloon catheters typically utilize markers at the distal end of the catheter, and at the first and second ends of the balloon. A balloon catheter used for embolic delivery will typically utilize markers at the distal end of the catheter, at the first and second ends of the balloon, and at a point 3 centimeters from the distal end.

Some methods utilizing radiopaque material may increase the external profile of particular sections of the catheter, making trackability through the vasculature more difficult. Some other methods may utilize a radiopaque material distributed over the majority of the catheter, which makes distinguishing proper sections of the catheter difficult.

A way to maximize visibility of proper sections of the catheter while limiting external profile of the catheter is thus beneficial.

SUMMARY OF THE INVENTION

A catheter is described with one or more markers on one or more sections of the device.

In one embodiment a catheter utilizing a marker element on one or more catheter sections is described In another embodiment, a catheter utilizing layered markers on one or more catheter sections is described.

BRIEF DESCRIPTION OF THE DRAWINGS

These and other aspects, features and advantages of the invention will be apparent and elucidated from the following description of embodiments of the present invention, reference being made to the accompanying drawings, in which.

DESCRIPTION OF EMBODIMENTS

Figure 1:
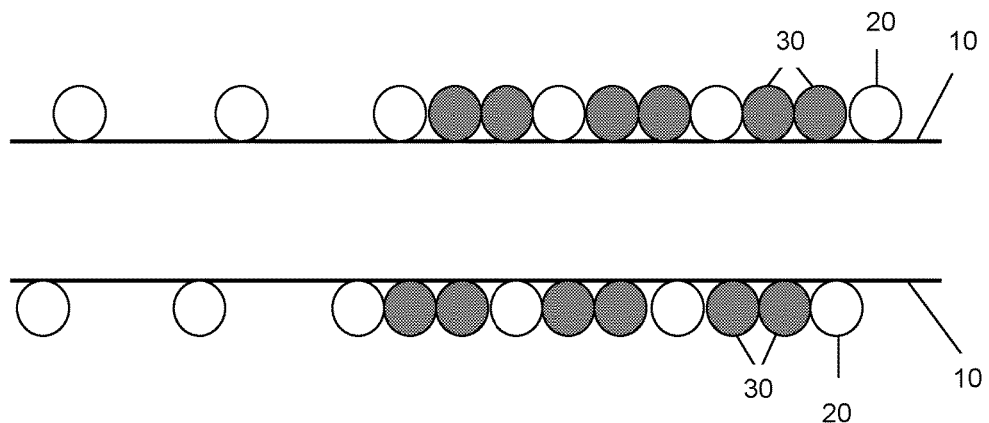
FIG. 1 is a cross-sectional view of a section of a catheter with an embodiment of a marker element of the invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

A catheter used to deliver embolic agents (i.e. embolic coils) typically includes markers at the distal end of the catheter and at a point 3 centimeters from the distal end to aid in imaging and coil delivery. A balloon catheter typically utilizes markers at the distal end of the catheter and at the first and second ends of the balloon. A balloon catheter used for embolic delivery will typically utilize markers at the distal end of the catheter, at the first and second ends of the balloon, and at and at a point 3 centimeters from the distal end. By means of example, the markers utilized here may be used on the catheter sections described above or various combinations therein. The figures illustrate one section of the catheter by way of illustrative example only, however, these configurations can exist on various sections of the catheter, such as those described above.

FIG. 1 illustrates a catheter having an inner layer 10, a reinforcement layer 20, and a marker element 30 which sits between the gaps of the reinforcement layer 20. The inner catheter layer 10 may be made of a polymer. The reinforcement layer 20 can be a coil, and helps increase the kink resistance of the catheter as it navigates the vasculature, although it may not necessarily be included with the marker elements 30. The reinforcement layer 20 may be a round wire, ribbon wire, elliptical wire, or various other shapes and may be made of stainless steel, nitinol, or similar materials. The marker element is made of a radiopaque material such as tantalum, gold, platinum, tungsten, other radiopaque materials, or combinations therein. The marker element may be a wound wire or coil. In the example where the reinforcement layer 20 is a coil and the marker element 30 is a coil, the marker element 30 would sit between the reinforcement layer filars. The marker element 30 may be the same size or slightly larger than the reinforcement layer coils 20. However, if a highly radiopaque material is used, the marker element 30 could conceivably be smaller than the reinforcement layer coils 20 and still achieve a good visibility profile.

Figure 2:
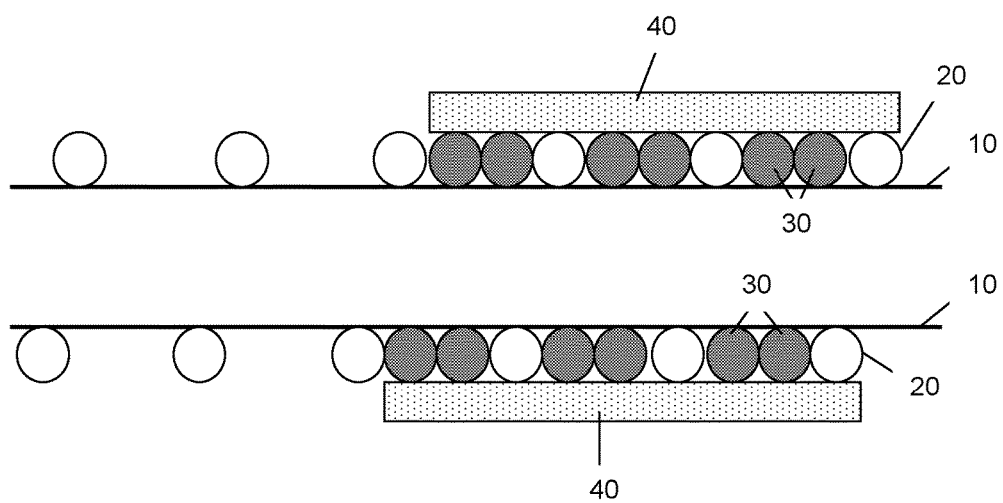
FIG. 2 is a cross-sectional view of a section of a catheter with an embodiment of a marker element of the invention.

FIG. 2 illustrates an alternative embodiment of a catheter having an inner layer 10, a reinforcement layer 20, a marker element 30 which sits between the gaps of the reinforcement layer 20 and a marker band 40 sitting over the marker element 30 and reinforcement layer 20. The inner catheter layer 10 may be made of a polymer. The reinforcement layer 20 may be a coil, and helps increase the kink resistance of the catheter as it navigates the vasculature, although it may not necessarily be included with the marker elements 30. The reinforcement layer 20 may be a round wire, ribbon wire, elliptical wire, or various other shapes and may be made of stainless steel, nitinol, or similar materials. The marker element 30 is made of a radiopaque material such as tantalum, gold, platinum, tungsten, other radiopaque materials, or combinations therein. The marker element 30 may be a wound wire or coil. In the example where the reinforcement layer 20 is a coil and the marker element 30 is a coil, the marker element 30 would sit between the reinforcement layer filars. The marker band 40 is also made of a radiopaque material such as tantalum, gold, platinum, tungsten, other radiopaque materials, or combinations therein. The marker band 40 is, in one example, a tube which sits over reinforcement layer 20 and marker elements 30. Similar to the previous embodiment, the marker element 30 may be the same size or slightly larger than the reinforcement layer coils 20, although depending on the radiopacity of the material used this may not necessarily be the case. Due to the presence of the marker element 30, the thickness of the marker band 40 necessary to achieve proper visibility may be smaller than if no marker coils were present.

Figure 3:
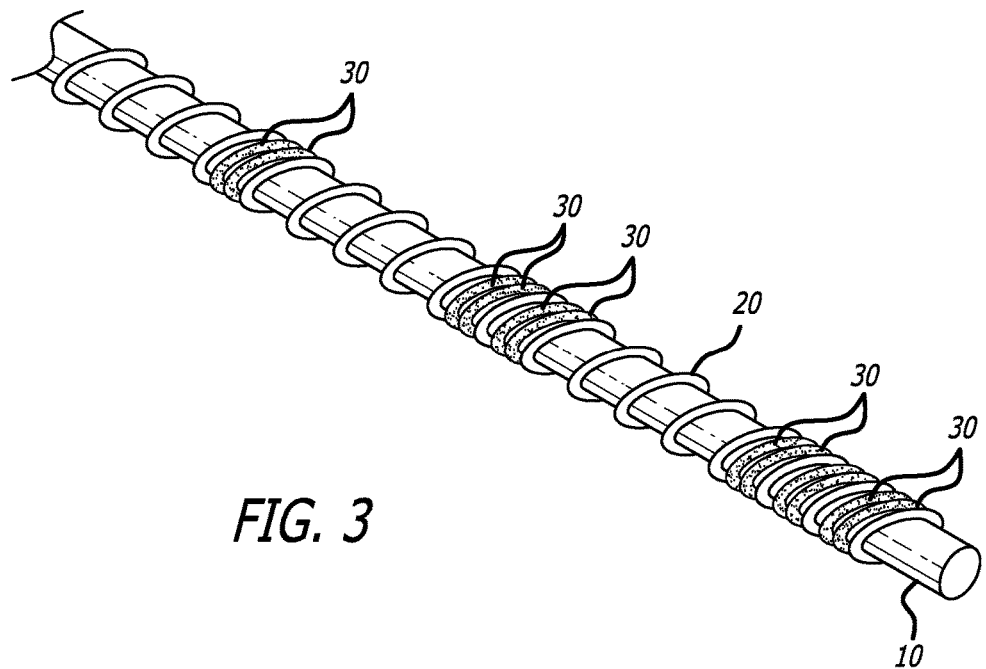
FIG. 3 is a perspective view of a section of a catheter with an embodiment of a marker element of the invention.

FIG. 3 depicts an embodiment including a catheter with a reinforcement layer 20 wrapped around an inner layer 10. Interspersed with the reinforcement layer 20 are multiple marker elements 30, axially spaced-apart along the inner layer 10.

Figure 4:
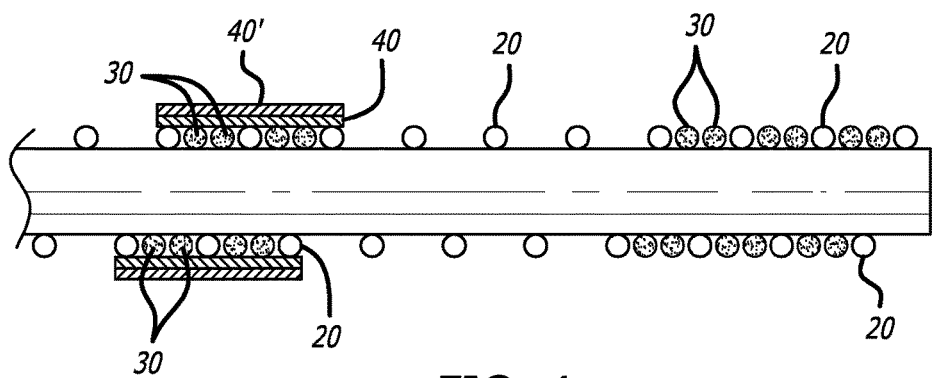
FIG. 4 is an elevation of a section of a catheter with an embodiment of a marker element of the invention with a cross-sectional depiction of layered marker bands.

FIG. 4 depicts an embodiment including a catheter with a reinforcement layer 20 wrapped around an inner layer 10. Also wrapped around the inner layer 10, and interspersed with the reinforcement layer 20, are two spaced-apart marker elements 30. Additionally shown is a marker band 40, with an additional marker band 40' wrapped around the marker band 40.

In another example, different sections of the device can use different combinations of markers (i.e. one part of the device can use the marker element 30, while another uses the marker element 30 and marker band 40), etc.

The following example of a configuration of a catheter utilizes the principles of the embodiments described above. It is only offered as an example and is not meant to overly restrict the designs that could be utilized with what is described. The particular example is used with an embolic delivery catheter with imaging segments at the distal tip and at a point 3 centimeters from the distal tip. This could be used with a balloon catheter where the imaging segments would be at the distal tip and the first and second ends of the balloon. This could also be used with an embolic delivery balloon catheter with imaging segments at the distal tip, at a point 3 centimeters from the distal tip, and at the first and second ends of the balloon. This could also be used in other imaging segment combinations.

As an example, a catheter can be comprised of four layers at a proximal section and either three or four layers at a distal end. The inner lumen of the catheter is surrounded by a first layer of lubricious polymer material. The first layer runs the full length of the device. The lubricious material preferably has a high melt temperature (greater than 500° F.). Some examples of materials are PTFE, polyimide loaded with PTFE and crosslinked PE. The inner jacket can be made of PTFE. The first layer of polymer material is surrounded by a reinforcement layer. The reinforcement layer (second layer) is comprised of a coil. The coil's purpose is to increase the kink resistance of the device. The reinforcement layer can run the full length of the device or terminate anywhere along the device. The coil assembly can be made up of a round wire, ribbon wire, elliptical wire, or any other type of shape. The purpose of the coil assembly is to prevent the catheter from kinking. The coil assembly is a round wire with a filar outer dimension of 0.001" and a coil pitch of 0.003" and the coil reinforcement extends the full length of the device. At the distal end of the coil reinforcement layer, there are two sections with round 0.001" platinum coil wound in between the stainless steel coil. In one case, the platinum coil is 0.001" with a 0.001" hollow tube marker band placed on top of the coil. Alternatively, the hollow tube marker band could be removed. The reinforcement layer is surrounded by a braided layer. The braid layer (third layer) is comprised of a woven wire pattern. The purpose of the braid is to increase the catheter stiffness in the proximal section. Just like the coil reinforcement, the braid can be made up of a round wire, ribbon wire, elliptical wire, or any other type of shape. The braid can extend the full length of the device or partially. In a particular example, the braid extends approximately 66% of the catheter length. The braid preferably has a low PIC (picks per inch) count to achieve the desired stiffness of the catheter, while the coil underneath the braid increases the kink resistance of the catheter. The fourth layer is the polymer jacket (outer layer). The outer layer of the outer assembly is preferably formed of longitudinally segmented, non-heat shrinkable, tubular elements. The individual segments may be fabricated from the same or different materials and may be attached to one another by welding, fusing, adhering, melting, or other polymerizing or non-polymerizing methods, or combinations thereof. The outer layer of the outer assembly may be fabricated from multiple different polymeric tubular segments. The outer layer of the outer assembly may be formed of a tubular polyamide such as Girlamid L25. A second more distal segment may be formed of a tubular polyether block amide such as Pebax 72D. A third more distal segment may be formed of a tubular polyether block amide such as Pebax 63D. A fourth more distal segment may be formed of a tubular polyether block amide such as Pebax 55D. A fifth more distal segment may be formed of a tubular polyether block amide such as Pebax 45D. A sixth more distal segment may be formed of a tubular polyblock amide such as Pebax 35D. A seventh more distal segment may be formed of a tubular polyblock amide such as Pebax 25D. The distal section of the catheter (3 centimeters) has at least one and possibly more marker bands between the reinforcement layer and the outer layer of polymer.

What is claimed is:

1. A method of marking a catheter comprising:
providing a catheter having:
an inner layer;
a reinforcement layer around said inner layer and constructed as an open, single-layer coil defining evenly-spaced gaps;
placing a marker element in said gaps of said reinforcement layer so as to not increase a thickness of the catheter; and,
placing at least one marker band around said catheter longitudinally aligned with said marker element and said reinforcement layer.

2. The method of claim 1 wherein providing a catheter with an inner layer and a reinforcement layer around said inner layer and constructed as an open, single-layer coil defining evenly-spaced gaps comprises providing a catheter with a reinforcement layer selected from the group consisting of round wire, ribbon wire, elliptical wire.

3. The method of claim 1 wherein providing a catheter with an inner layer and a reinforcement layer around said inner layer and constructed as an open, single-layer coil defining evenly-spaced gaps comprises providing a catheter with a reinforcement layer of a material selected from the group consisting of stainless steel and Nitinol.

4. The method of claim 1 wherein said marker element comprises a material selected from the group consisting of tantalum, gold, platinum, tungsten, and radiopaque alloys.

5. The method of claim 1 wherein placing a marker element in said gaps of said reinforcement layer so as to not increase a thickness of the catheter comprises placing a coil in said gaps.

6. The method of claim 1 wherein placing at least one marker band around said catheter longitudinally aligned with said marker element and said reinforcement layer comprises placing a first marker band around said reinforcement layer.

7. The method of claim 6 wherein placing at least one marker band around said catheter longitudinally aligned with said marker element and said reinforcement layer comprises placing at least one additional marker band around said first marker band.

8. The method of claim 1 further comprising placing at least one additional marker element between said gaps of said reinforcement layer.

9. The method of claim 1 wherein placing at least one marker band around said catheter longitudinally aligned with said marker element and said reinforcement layer comprises placing at least one marker band around at least one of said marker elements.

10. A method of marking a catheter comprising:
providing a catheter having:
an inner layer;
at least one reinforcement coil wrapped around said inner layer to form an open, evenly spaced coil;
wrapping at least one marker coil around said inner layer and interspersed with said at least one reinforcement coil such that said marker coil does not increase a thickness of the catheter; and,
placing at least one circumferential marker band around said catheter such that the circumferential marker band is longitudinally aligned with said marker coil and said reinforcement coil.

11. The method of claim 10 wherein placing at least one circumferential marker band around said catheter comprises placing a first marker band around said reinforcement layer.

12. The method of claim 11 wherein placing at least one circumferential marker band around said catheter comprises placing at least one additional marker band disposed around said first marker band.

13. The method of claim 10 wherein wrapping at least one marker coil around said inner layer comprises interspersing said marker coil within said reinforcement coil such that filars of said coils are arranged in a repeating marker-marker-reinforcement pattern.

14. The method of claim 10 wherein wrapping at least one marker coil around said inner layer comprises wrapping a marker coil with filars having diameters that are unequal to diameters of filars of said reinforcement coil.

* * * * *